United States Patent [19]

Hickmann et al.

[11] Patent Number: 5,245,042
[45] Date of Patent: Sep. 14, 1993

[54] PREPARATION OF CIS-2-(1H-1,2,4-TRIAZOL-1-YLMETHYL)-2-(HALOPHENYL)-3-(HALOPHENYL) OXIRANE

[75] Inventors: Eckhard Hickmann, Dannstadt; Rainer Seele; Reiner Kober, both of Fussgoenheim; Heinz Isak, Mutterstadt, all of Fed. Rep. of Germany

[73] Assignee: BASF Aktiengesellschaft, Ludwigshafen, Fed. Rep. of Germany

[21] Appl. No.: 874,227

[22] Filed: Apr. 27, 1992

Related U.S. Application Data

[63] Continuation of Ser. No. 600,715, Oct. 22, 1990, abandoned.

[30] Foreign Application Priority Data

Nov. 4, 1989 [DE] Fed. Rep. of Germany ....... 3936821

[51] Int. Cl.$^5$ ............................................ C07D 249/08
[52] U.S. Cl. .................................................. 548/268.8
[58] Field of Search ...................................... 548/268.8

[56] References Cited

U.S. PATENT DOCUMENTS 4,464,381  8/1984  Janssen et al. ...................... 514/383
4,906,652  3/1990  Karbach et al. .................... 514/383

OTHER PUBLICATIONS

Mar., "Advanced Organic Chemistry", 2nd Ed. 1977 NY McGraw-Hill p. 1132.

*Primary Examiner*—Patricia L. Morris
*Attorney, Agent, or Firm*—Oblon, Spivak, McClelland, Maier & Neustadt

[57] ABSTRACT

A process is described for the preparation of cis-2-(1H-1,2,4-triazol-1-ylmethyl)-2-(halophenyl)-3-(halophenyl)oxirane I

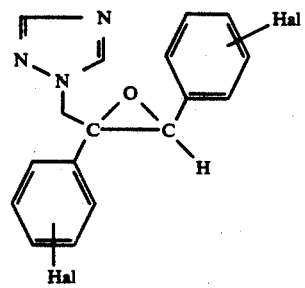

by epoxidizing Z-3-(1H-1,2,4-triazol-1-yl)-2-(halophenyl)-1-halophenyl)propene II,

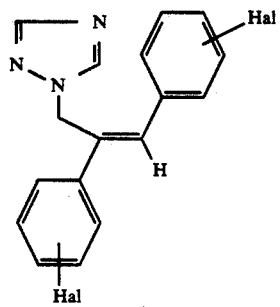

where halogen is in each case fluorine, chlorine or bromine, which comprises reacting the crude product of the epoxidation with one or more reducing agents, which are added to the reaction mixture in a considerable excess over the amount necessary to destroy any peroxide compounds present.

10 Claims, No Drawings

PREPARATION OF CIS-2-(1H-1,2,4-TRIAZOL-1-YLMETHYL)-2-(HALOPHENYL)-3-(HALOPHENYL) OXIRANE

This application is a continuation of application Ser. No. 07/600,715, filed on Oct. 22, 1990, now abandoned.

The present invention relates to a process for the preparation of cis-2-(1H-1,2,4-triazol-1-ylmethyl)-2-(halophenyl)-3-(halophenyl)oxirane I

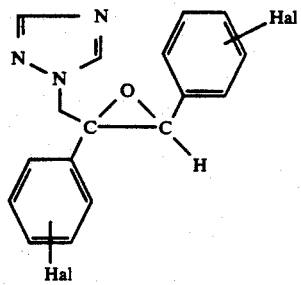

by epoxidizing Z-3-(1H-1,2,4-triazol-1-yl)-2-(halophenyl)-1-(halophenyl)propene II,

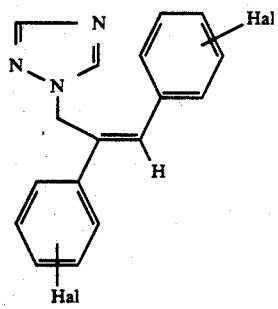

where halogen is in each case fluorine, chlorine or bromine.

The preparation of epoxides of structure I is described, for example, in German Laid-Open Applications DE-OS 32 18 129 and 32 18 130 and in EP-A-196 038.

After an epoxidation of an olefin using peroxide compounds, such as hydrogen peroxide, alkyl hydroperoxides, dialkyl peroxides, peroxycarboxylic acids or diacyl peroxides, any residues of the latter present in the crude reaction mixture are usually destroyed, for example on a noble-metal catalyst (usually Pt or Pd) or by adding a chemical reducing agent. This aftertreatment of the crude products of epoxidation reactions is carried out for purely safety reasons, i.e. to ensure that the peroxide compounds, which are without exception high in energy, cannot decompose in an uncontrolled, disastrous manner during further work-up. For the purposes of the invention, peroxide compounds are, for example, inorganic and organic peroxides, hydroperoxides and peracids.

It is an object of the present invention to prevent unsatisfactory yields in the epoxidation of olefins II and the associated high purification costs.

We have found that this object is achieved by a process for the preparation of cis-2-(1H-1,2,4-triazol-1-ylmethyl)-2-(halophenyl)-3-(halophenyl)oxirane I

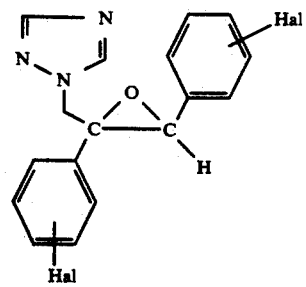

by epoxidizing Z-3-(1H-1,2,4-triazol-1-yl)-2-(halophenyl)-1-(halophenyl)propene II,

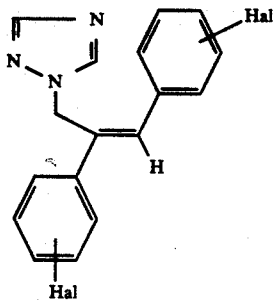

where halogen is in each case fluorine, chlorine or bromine, using a peroxide compound, which comprises reacting the crude product of the epoxidation with one or more reducing agents, which are added to the reaction mixture in a considerable excess over the amount necessary to destroy any peroxide compounds present.

The surprising yield- and purity-improving action of reducing agents in the present process according to the invention is only observed if they are employed in excess, i.e. more is added than necessary for the rapid reduction of surviving peroxide compounds, the amount of which can be determined in a conventional manner, for example by iodometric titration. If, by contrast, the reaction batches, after catalytic or reductive destruction of the residual peroxide compounds, are worked up without reductive aftertreatment of the peroxide-free crude product, maximum yields of 65% of theory are obtained in the crude product (see comparative examples). Target-product losses in the purification operations which are necessary, for example during crystallization, reduce the isolated yield of target product to a maximum of 50% of theory.

A wide range of reducing agents and reduction processes are suitable for the reductive aftertreatment according to the invention, for example catalytic hydrogenation on catalysts, e.g. Pt, Pd or Raney nickel, transfer hydrogenation using, for example, ammonium formate on palladium, reductions using hydrogen in statu nascendi, e.g. zinc/glacial acetic acid, iron/hydrochloric acid or aluminum/sodium hydroxide solution, reductions using complex metal hydrides, e.g. sodium borohydride, sodium dimethoxyborohydride or sodium triacetoxyborohydride, reduction using element hydrides, e.g. diborane, reduction using salts of metals in low oxidation states, e.g. tin(II) chloride, iron(II) sulfate or titanium(III) chloride, reductions using compounds of elements from main groups 5 and 6 of the periodic table in low oxidation states, e.g. hydrazine, hydroxylamine, trimethyl phosphite, triphenylphosphine, phosphorus trichloride, hydrophosphites, thionyl chloride, sulfur dioxide, hydrogen sulfites, disulfites, dithionites, thiosulfates, sulfinates; hydrogen sulfides and sulfides, reduction using reducing organic compounds, e.g. formaldehyde, glyoxal, glyoxylic acid, formic acid, α-hydroxysulfinic acids, α-hydroxysulfonic acids and salts thereof, e.g. alkali metal or alkaline earth metal-α-hydroxyalkylsulfonate or -sulfinate.

Particular preference is given to reductive aftertreatment by catalytic hydrogenation using sulfites, hydrogen sulfite, disulfite or dithionite.

The reducing agent additionally used in excess to reduce the amounts of residual peroxide is employed in amounts of from about 10 mol-% to about 2000 mol-%, preferably from about 50 mol-% to about 1500 mol-%, based on Z-3-(1H-1,2,4-triazol-1-yl)-2-(halophenyl)-1-(halophenyl)propene II.

The reductive aftertreatment can be carried out in one or more steps. For example, the residual peroxide compounds can first be reduced or decomposed on a noblemetal catalyst, and then treated with a reducing agent, if desired a different one, in the abovementioned excess amounts, or the two operations can be combined in one.

The treatment with excess reducing agent is expediently carried out in the presence of the solvent used for the epoxidation, and the reaction mixture may comprise one or more phases. However, it is also possible to change the solvent, preferably after destruction of the residual peroxide compounds, if the reducing agent is incompatible with the solvent for the epoxidation.

Examples of suitable solvents for the reductive aftertreatment are aromatic hydrocarbons, e.g. benzene, toluene and xylenes; ether, e.g. tert-butyl methyl ether and diethylene glycol dimethyl ether; chlorinated hydrocarbons, e.g. methylene chloride, 1,2-dichloroethane, 1,1,1-trichloroethane and chlorobenzene; alcohols, e.g. methanol, isopropanol, sec- and tert-butanol and ethylene glycol; carboxylic acids, e.g. acetic acid and propionic acid; esters, e.g. ethyl acetate, i-amyl acetate, methyl butyrate and dimethyl succinate; amides, e.g. dimethylformamide and N-methylpyrrolidone; nitriles, e.g. acetonitrile, ureas, e.g. N,N,N',N'-tetramethylurea, N,N'-dimethylethyleneurea and N,N'-dimethylpropyleneurea; water, and single- and multiphase mixtures of these. In general, the reducing agents are selected so that they do not themselves react with the solvent. However, they can also be intentionally combined so that the active reducing agent is only formed in situ, e.g. diborane from sodium borohydride and methylene chloride, and sodium dimethoxyborate from sodium borohydride and methanol.

The reaction temperature during the reductive aftertreatment is generally from 0° to 150° C., preferably from 20° to 80° C.

The reaction generally takes from 0.5 to 10 hours, preferably from 1 to 3 hours.

In the reductive aftertreatment, the preferred pH depends on the known optimum of the particular reducing agent. Thus, sodium dithionite or sodium hydroxymethylsulfinate are used in the alkaline pH range, and sodium hydrogen sulfite in the acidic range.

The cis-2-(1H-1,2,4-triazol-1-ylmethyl)-2-(halophenyl)-3-(halophenyl)oxirane I is isolated by conventional methods, e.g. by filtration, centrifugation or, if necessary after phase separation, by precipitation, crystallization or evaporation. For purification, washing or digestion with water is generally sufficient. To prepare high purity products, digestion or recrystallization using an organic solvent (mixture) can be carried out instead of or in addition to the above.

The epoxidation reaction itself is carried out in a conventional manner, for example as described in the prior art cited at the outset. Under the conditions indicated therein or appropriately modified conditions, the olefins II are oxidized using peroxycarboxylic acids, such as perbenzoic acid, 3-chloroperbenzoic acid, 4-nitroperbenzoic acid, monoperphthalic acid, peracetic acid; perpropionic acid, permaleic acid, monoperisuccinic acid, perpelargonic acid or trifluoroperacetic acid, in inert solvents, preferably chlorinated hydrocarbons, e.g. methylene chloride, chloroform, carbon tetrachloride or dichloroethane, or, if desired, in acetic acid, ethyl acetate or dimethylformamide, if desired in the presence of a buffer, such as sodium acetate, sodium carbonate, sodium hydrogen carbonate or disodium hydrogen phosphate. The reaction is carried out at from 10° to 100° C. and catalyzed, if desired, by iodine, sodium tungstate or light.

The epoxidation is preferably carried out in the presence of a large excess of peracid, e.g. permaleic acid, which is advantageously prepared in situ from 5 to 30 mol equivalents, in particular from 5 to 10 mol equivalents of maleic anhydride, based on the olefin II, and less than stoichiometric amounts of hydrogen peroxide solution, based on the maleic anhydride. In general, anhydride:$H_2O_2$ molar ratios of from 1.5 to 10, in particular from 2 to 4, are employed. A 30 to 50% strength aqueous solution of hydrogen peroxide can advantageously be used.

The reaction temperature for the epoxidation can be from 0° to 100° C., in particular from 20° to 80° C.

The examples below illustrate the process according to the invention, which can also be applied to other azolylmethyl stilbenes.

EXAMPLE 1

58.9 g (0.601mol) of maleic anhydride and 18.6 g of 97.2% (0.0576mol) Z-3-(1H-1,2,4-triazol-1-ylmethyl)-2-(fluorophenyl)-1-(2-chlorophenyl)propene are dissolved at 40° C. in 150ml of 1,2-dichloroethane, 20.6 g (0.303 mol) of 50% strength aqueous hydrogen peroxide solution are added dropwise at a uniform rate over the course of 1 hour, and the reaction mixture is stirred at 40° C. for 7 hours. A sample taken while stirring contains 0.4% of peroxide compounds, calculated as hydrogen peroxide, on iodometric titration; this requires 6.9 ml of 38% strength sodium hydrogen sulfite solution to reduce the peroxide compounds. 100 ml of water are added, the aqueous phase is buffered at pH 3 using 50% strength sodium hydroxide solution, and 170 ml of 38% strength sodium hydrogen sulfite solution are added, corresponding to an excess of 1385 mol-%, based on the olefin employed, and the two-phase reaction mixture is stirred vigorously at 50° C. for 3 hours. The aqueous phase is neutralized using 50% strength sodium hydroxide solution, and about 94% of the 1,2-dichloroethane employed are recovered by azeotropic distillation at atmospheric pressure (azeotrope boiling point: 72° C.). The cis-2-(1H-1,2,4-triazol-1-ylmethyl)-2-(4-fluorophenyl)-3-(2-chlorophenyl)oxirane which crystallizes out completely on cooling the aqueous phase which remains is separated off, washed thoroughly with water and dried at 90° C. under reduced pressure, giving 17.7 g of product with a purity of 93.4%, determined by quantitative high-pressure liquid chromatography (HPLC). This corresponds to a yield of 87% of theory.

EXAMPLE 2

The epoxidation is carried out as described in Example 1, the maleic acid, most of which precipitates out after cooling, is filtered off, the filter cake is washed with a little 1,2-dichloroethane, and the filtrate and washings are combined. This crude product solution weighs 242 g and contains, according to iodometric titration, 0.08% of peroxide compounds, calculated as hydrogen peroxide. This requires 0.99 g of sodium dithionite to reduce the per-compounds. 12.0 g of sodium dithionite in 40 ml of water, corresponding to an excess of 110 mol-%, based on the olefin employed, are added, the two-phase reaction mixture is stirred at from 70° to 75° C. for 3 hours, and the organic phase is worked up, to give 18.0 g of cis-2-(1H-1,2,4-triazol-1-ylmethyl)-2-(4-fluorophenyl)-3-(2-chlorophenyl)oxirane in a purity of 95.2% (quantitative HPLC), corresponding to a yield of 90.2% of theory.

EXAMPLE 3

By a method similar to that of Example 1, a mixture of 9.3g of 97.2% (0.0288mol) Z-3-(1H-1,2,4-triazol-1-ylmethyl)-2-(4-fluorophenyl)-1-(2-chlorophenyl)propene, 55 ml of 1,2-dichloroethane, 28 g of maleic anhydride, 0.3 g of 2,6-di-tert-butylphenol and 7.3 g of 50% strength hydrogen peroxide is stirred at 50° C. for 6hours and at 70° C. for a further 2 hours. The small amount of peroxide compounds remaining is destroyed by adding a 10% strength aqueous sodium thiosulfate solution, the reaction mixture is neutralized using 50% strength sodium hydroxide solution, the organic phase is separated off and evaporated, the residue is dissolved in 70 ml of methanol, 0.5 g of Raney nickel is added, and the mixture is stirred at 50° C. for 2 hours under 2 l of hydrogen (corresponding to 310 mol-%, based on the olefin employed). The catalyst is filtered off, and the solution is evaporated to give 8.9 g of cis-2-(1H-1,2,4-triazol-1-ylmethyl)-2-(4-fluorophenyl)-3-(2-chlorophenyl)oxirane in a purity of 94.1% (quantitative HPLC), corresponding to a yield of 88.2% of theory.

COMPARATIVE EXAMPLES

Comparative Example 1

The epoxidation is carried out as described in Example 1, the residual peroxide compounds are reduced using the stoichiometric amount of 38% strength sodium hydrogen sulfite solution (8.2 ml), and the mixture is worked up without reductive aftertreatment with excess bisulfite solution, giving 17.2 g of crude product containing 70.4% of cis-2-(1H-1,2,4-triazol-1-ylmethyl)-2-(4-fluorophenyl)-3-(2-chlorophenyl)oxirane (quantitative HPLC), corresponding to a yield of 63.7% of theory.

Comparative Example 2

The epoxidation is carried out in the same manner as in Example 2, the residual peroxide compounds are destroyed using the stoichiometric amount of sodium dithionite (1.4 g), but without reductive aftertreatment with excess dithionite solution, to give 17.5 g of crude product containing 66.7% of cis-2-(1H-1,2,4-triazol-1-ylmethyl)-2-(4-fluorophenyl)-3-(2-chlorophenyl)oxirane, corresponding to a yield of 61.4% of theory.

Comparative Example 3

The procedure is as described in Example 3, but the reductive aftertreatment of the peroxide-free crude product with hydrogen and Raney nickel is omitted. 8.6 g of crude product containing 65.6% of cis-2-(1H-1,2,4-triazol-1-ylmethyl)-2-(4-fluorophenyl)-3-(2-chlorophenyl)oxirane, corresponding to a yield of 59.4% of theory, are obtained.

We claim:

1. A process for preparing cis-2-(1H-1,2,4-triazol-1-ylmethyl)-2-(halophenyl)-3-(halophenyl) oxirane of the formula (I):

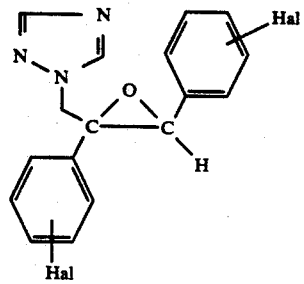

which comprises:
a) epoxidizing Z-3-(1H-1,2,4-triazol-1-yl)-2-(halophenyl)-1-(halophenyl) propene of the formula (II):

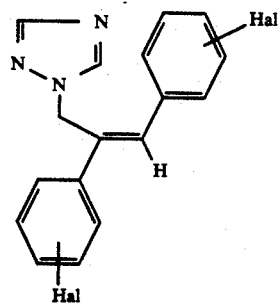

wherein Hal is independently fluorine, chlorine or bromine, with a peroxide compound capable of effecting said epoxidation reaction and being selected from the group consisting of perbenzoic acid, 3-chloroperbenzoic acid, 4-nitroperbenzoic acid, monoperphthalic acid, peracetic acid, perpropionic acid, permaleic acid, monopersuccinic acid, perpelargonic acid and trifluoroperacetic acid; and b) reacting the crude product of the epoxidation reaction with one or more reducing agents, which are capable of destroying any peroxide compounds present, and which are selected from the group consisting of:
(i) catalytic hydrogenation on catalysts, which is selected from the group consisting of hydrogenation on Pt, Pd and Raney-Ni, and transfer hydrogenation using ammonium formate on Pd;

ii) a reducing agent selected from the group consisting of zinc/glacial acetic acid, iron/hydrochloric acid and aluminum/sodium hydroxide solution;

iii) complex metal hydrides selected from the group consisting of sodium borohydride, sodium dimethoxyborohydride and sodium triacetoxyborohydride;

iv) a reducing agent which is diborane;

v) salts of metals in low oxidation states selected from the group consisting of tin (II) chloride, iron (II) sulfate and titanium (III) chloride;

vi) compounds of elements from main groups V and VI of the Periodic Table in low oxidation states which are selected from the group consisting of hydrazine, hydroxylamine, trimethylphosphite, triphenylphosphene, phosphorus trichloride, hydrophosphites, thionyl chloride, sulfur dioxide, hydrogen sulfites, disulfites, dithionates, thiosulfates, sulfinates, hydrogen sulfides and sulfides;

vii) reducing organic compounds selected from the group consisting of formaldehyde, glyoxyl, glyoxylic acid, formic acid, α-hydroxylsulfinic acids, α-hydroxysulfonic acids and alkali metal or alkaline earth metal salts thereof and α-hydroxyalkyl sulfonates and -sulfinates; and viii) a reducing agent selected from the group consisting of catalytic hydrogenation using sulfites, hydrogen sulfites, disulfites and dithionates; and which reducing agents are added to the reaction mixture in a substantial excess over the amount necessary to destroy any peroxide compounds present.

2. The process as claimed in claim 1, wherein said epoxidation reaction is carried out at from 0° C. to 100° C.

3. The process as claimed in claim 1, which further comprises catalyzing said epoxidation reaction with iodine, sodium tungstate or light.

4. The process as claimed in claim 2, wherein said epoxidation reaction is carried out at from 20° C. to 80° C.

5. The process as claimed in claim 1, wherein said peroxide compound capable of effecting said epoxidation reaction is used in an amount in excess of the amount of said olefin of the formula (II) used.

6. The process as claimed in claim 5, wherein said 5 to 30 mol equivalents of said peroxide compound are used based upon the olefin of the formula (II).

7. The process as claimed in claim 6, which further comprises subjecting said crude product to a reductive after treatment using hydrogen or a hydrogen donor and a metallic catalyst selected from the group consisting of Ni, Co, Pt and Pd either before or with said reaction of said crude product with said one or more reducing agents.

8. The process as claimed in claim 1, wherein the one or more reducing agents are used in an amount of from about 10–1500 mol % based on the amount of 2,3-(1H-1,2,4-triazol-1-yl)-2-(halophenyl)-1-(halophenyl) propene used.

9. The process as claimed in claim 7, wherein the reductive aftertreatment is carried out at from 20° to 80° C.

10. The process as claimed in claim 1, wherein cis-2-(1H-1,2,4-triazol-1-ylmethyl)-2-(4-fluorophenyl)-3-(2-chlorophenyl)oxirane is prepared.

* * * * *